US012640256B2

(12) United States Patent
Keller

(10) Patent No.: US 12,640,256 B2
(45) Date of Patent: May 26, 2026

(54) SYSTEMS AND METHODS FOR SHARING HEALTHCARE DATA WITH HEALTHCARE DATA PROCESSORS

(71) Applicant: Roche Diagnostics Operations, Inc., Indianapolis, IN (US)

(72) Inventor: Stefan Keller, Basel (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 289 days.

(21) Appl. No.: 18/484,066

(22) Filed: Oct. 10, 2023

(65) Prior Publication Data

US 2024/0127942 A1 Apr. 18, 2024

(30) Foreign Application Priority Data

Oct. 13, 2022 (EP) .................................... 22201342

(51) Int. Cl.
 G16H 40/20 (2018.01)
 G16H 10/60 (2018.01)
 (Continued)

(52) U.S. Cl.
 CPC ............. G16H 40/20 (2018.01); G16H 10/60 (2018.01); H04L 9/088 (2013.01); H04L 9/30 (2013.01)

(58) Field of Classification Search
 CPC ........ G16H 40/20; G16H 10/60; H04L 9/088; H04L 9/30
 See application file for complete search history.

(56) References Cited

U.S. PATENT DOCUMENTS 9,378,380 B1 6/2016 Reid et al.
9,819,650 B2 11/2017 Soon-Shiong et al.
(Continued)

FOREIGN PATENT DOCUMENTS

EP 3422221 A1 1/2019
EP 3477903 A1 5/2019
(Continued)

OTHER PUBLICATIONS

European Search Report issued Mar. 21, 2023 in Application No. 22201342.7, 2 pp.

*Primary Examiner* — Fonya M Long
*Assistant Examiner* — Anthony Balaj
(74) *Attorney, Agent, or Firm* — Lee & Hayes, P.C.

(57) ABSTRACT

A computer implemented method for a data sharing system to share healthcare data from a healthcare data provider with a healthcare data processing application. The method includes identifying one or more healthcare data processor applications, generating and displaying selectable options of the one or more data processor applications at a healthcare data provider, obtaining a selection of the one or more data processor applications from the healthcare data provider, obtaining a data provider/application-specific encryption keyset corresponding to each selected healthcare data processor application, the keyset comprising a private key and a public key, retaining the private key of the data provider/application-specific keyset with a trusted component of the healthcare data provider, and sharing the public key of the data provider/application-specific keyset with the corresponding selected healthcare data processor application.

20 Claims, 8 Drawing Sheets

(51) Int. Cl.
    *H04L 9/08*           (2006.01)
    *H04L 9/30*           (2006.01)

(56)               References Cited

U.S. PATENT DOCUMENTS

| | | | |
|---|---|---|---|
| 2011/0010759 A1 | 1/2011 | Adler | |
| 2014/0181517 A1* | 6/2014 | Alaranta | H04L 63/062 |
| | | | 713/168 |
| 2014/0244296 A1* | 8/2014 | Linn | G16H 40/20 |
| | | | 705/3 |
| 2016/0337326 A1* | 11/2016 | O'Hare | H04L 9/0844 |
| 2017/0085535 A1* | 3/2017 | Gross | H04L 9/321 |
| 2018/0076954 A1* | 3/2018 | Mesiano | H04L 9/0822 |
| 2019/0036688 A1 | 1/2019 | Wasily et al. | |
| 2020/0204361 A1 | 6/2020 | Fries et al. | |
| 2020/0311289 A1* | 10/2020 | Cooper | G06F 21/602 |
| 2020/0402625 A1* | 12/2020 | Aravamudan | G06F 21/6245 |

FOREIGN PATENT DOCUMENTS

| | | | |
|---|---|---|---|
| EP | 3629274 A1 | 4/2020 | |
| WO | 2002/005061 A2 | 1/2002 | |

* cited by examiner

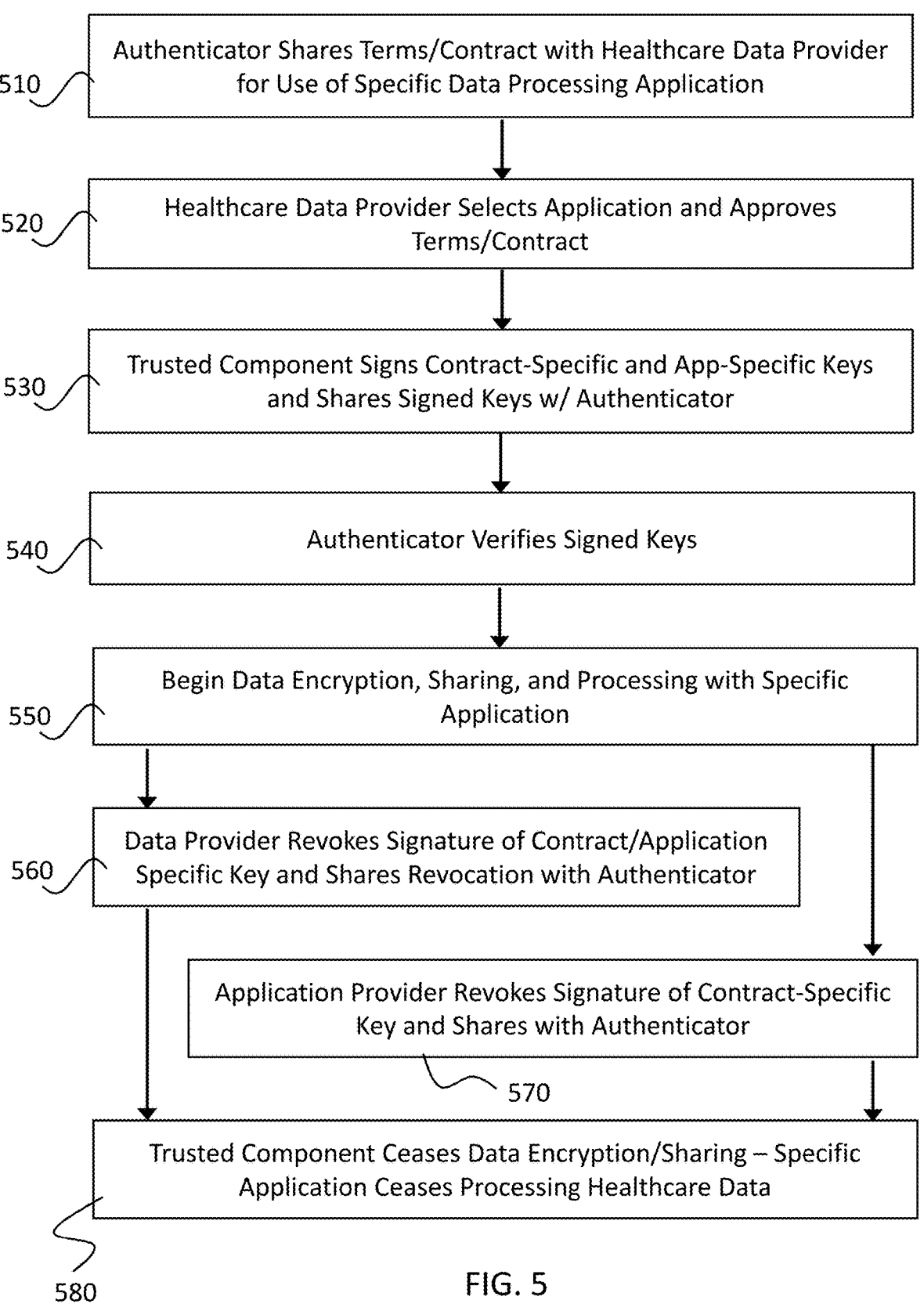

510 — Authenticator Shares Terms/Contract with Healthcare Data Provider for Use of Specific Data Processing Application 520 — Healthcare Data Provider Selects Application and Approves Terms/Contract 530 — Trusted Component Signs Contract-Specific and App-Specific Keys and Shares Signed Keys w/ Authenticator 540 — Authenticator Verifies Signed Keys 550 — Begin Data Encryption, Sharing, and Processing with Specific Application 560 — Data Provider Revokes Signature of Contract/Application Specific Key and Shares Revocation with Authenticator 570 — Application Provider Revokes Signature of Contract-Specific Key and Shares with Authenticator 580 — Trusted Component Ceases Data Encryption/Sharing – Specific Application Ceases Processing Healthcare Data

FIG. 5

SYSTEMS AND METHODS FOR SHARING HEALTHCARE DATA WITH HEALTHCARE DATA PROCESSORS

CROSS-REFERENCE TO RELATED APPLICATIONS

This application claims priority to European Patent Application No. 22201342.7, filed Oct. 13, 2022, the disclosure of which is hereby incorporated by reference in its entirety.

BACKGROUND

Processing electronic healthcare data is a critical aspect of providing effective healthcare services. Healthcare data processing can include analyzing individual patient records for identifying biomarkers and/or physiological variables to make diagnosis and/or to identify the most effective treatments. Other processing functions include analyzing volumes of patient records to identify trends in the data and correlate particular biomarkers/physiological variables with diseases and/or effective treatments. Further processing functions include organizing and reorganizing healthcare data (e.g., in a structured electronic database) for efficient future access by healthcare providers and researchers.

Many independent data processors offer healthcare data processing services and products to healthcare providers and research institutions. While these independent platforms offer important services, of significant importance is maintaining the security and confidentiality of the shared healthcare records. These independent platforms may each offer different degrees of data processing functionality, terms of service, security, and sensitivity in the records they process, including on an application-by-application basis through the same healthcare data processor/consumer. It may be difficult for a healthcare data provider (e.g., a hospital) to assess the security and risks involved with sharing healthcare data with particular healthcare data processors and their products/applications, particularly when shared across large networks such as the internet.

Some healthcare data consumers merely provide security by utilizing/sharing their own encryption keys or using a generally available encryption platform (e.g., a web browser). In some cases, after the use of a particular data processor by a healthcare data provider, the healthcare provider may no longer wish to share its data, a license for the use of the data consumer expires, the terms of use change, and/or the security functionality (e.g., encryption certificate) may have expired. However, the channel with which healthcare data is shared may still be left active, without intending to be shared or processed, sensitive healthcare data may continue to be routed and processed by a data processor. Secure, trusted, and proactive systems and methods for sharing healthcare data between healthcare data providers and the variety of available healthcare data processors and their applications/services are thus needed.

SUMMARY

Aspects of the invention provide a system for healthcare data providers, including hospital systems and other providers, to access and securely share their healthcare data with multiple external/independent healthcare processing applications. The system, including an authenticator, may identify, confirm terms of engagement, and securely share sensitive healthcare data from the provider on an application-by-application processing basis. The system provides an interface for a healthcare data provider to select a specific application with which it securely shares data and accesses the results of the processing. The system arranges the sharing of encryption keys respective to the healthcare data provider and specific healthcare data processing application. Sharing and processing of healthcare data is activated by way of the system receiving and verifying signed keys respective to the healthcare data provider and processing application. The process of signing and sharing signed keys using the system may be accomplished with a trusted component that may be integrated with the healthcare data provider to ensure validity of the application/signatures by an authentication service and the healthcare data provider. Termination of the processing may be accomplished by way of the healthcare data provider or processor revoking its signature/authorization with the authenticator.

When each of respective keys are signed, the trusted component obtains applicable healthcare data and utilizes a public key to encrypt the data and share the encrypted data with the data processor/specific application. The specific application may utilize a private key to decrypt the data, after which it processes the unencrypted data and can transmit processed results to the healthcare data provider.

In some embodiments, terms of use or a contract/agreement are associated with a specific data processing application. The system obtains the terms/contract/agreement and shares the contract/terms/agreement with the data provider, which authorizes the terms/contract/agreement by signing a key respective to the specific provider, application and/or specific contract, and which is then shared with the system (e.g., with the authenticator using the trusted component). The healthcare data provider and/or data processor/application can terminate healthcare data processing (including encryption/sharing) by alerting the system (e.g., authenticator) that the terms/contract/agreement have been revoked.

In some embodiments, the system authorizes sharing of healthcare data on a specific dataset basis (e.g., in addition to being based per a specific provider, application, and contract/terms). A data provider may authorize or revoke the sharing of one or more specific sets of data (e.g., data files). A data provider may, for example, choose to add or remove sets of data for sharing with a specific data processing application with specific terms of use (e.g., contract/agreement/terms). A particular keyset used for encrypting/decrypting healthcare data may then be associated with that selected data for use with the respective data processing application/contract. The data provider may thereby restrict data for encryption/sharing with the data processing application and/or contract/terms to the selected datasets.

Some embodiments include a computer implemented method for a data sharing system to share healthcare data from a healthcare data provider with a healthcare data processor, the method comprising:

- identifying one or more healthcare data processor applications;
- generating and displaying selectable options of the one or more data processor applications at a healthcare data provider;
- obtaining a selection of the one or more data processor applications from the healthcare data provider;
- obtaining a data provider/application-specific encryption keyset corresponding to each selected healthcare data processor application, the keyset comprising a private key and a public key;
- retaining the private key of the data provider/application-specific keyset with a trusted component of the healthcare data provider;

sharing the public key of the data provider/application-specific keyset with the corresponding selected healthcare data processor application;

at an authentication server of the healthcare data sharing system, authenticating and validating the public key of the data provider/application-specific keyset as being signed and validated using the trusted component of the healthcare data provider and being signed and validated by the respective selected data processor application;

when the public key of the data provider/application-specific keyset is authenticated and validated for both the healthcare data provider and the corresponding data processor application, causing the healthcare data of the healthcare data provider to be encrypted using the private key of the corresponding data provider/application-specific keyset, and causing the encrypted healthcare data to be transmitted to the corresponding selected data processor application.

In some embodiments, sharing the public key of the data provider/application-specific keyset comprises:

signing the public key using the trusted component; and transmitting the signed public key to the corresponding selected data processor application.

In some embodiments, the method comprises:

transmitting the signed public key to the authentication server;

at the authentication server, storing a record of receiving the signed public key in order to authenticate and validate the public key of the data provider/application-specific keyset as being signed and validated by the respective data provider.

In some embodiments, the method further comprises:

at the authentication server, receiving a communication from one of the healthcare data provider or the data processor application indicating that the data provider/application-specific keyset is no longer validated; and, ceasing to cause the encrypted healthcare data to be transmitted to the corresponding selected data processor application.

In some embodiments, the data provider/application-specific keyset is also terms-specific, the terms pertaining to an agreement for use of the healthcare data and the data processor application.

In some embodiments, the method comprises: obtaining a set of terms relating to use of the corresponding selected data processor application; providing to the healthcare data provider a selectable option for accepting the set of terms; obtaining a selection of the option for accepting the set of terms; and, in response to obtaining a selection accepting the set of terms by the healthcare data provider, causing the public key of the data provider/application-specific and terms-specific keyset to be signed using the trusted component of the healthcare data provider.

In some embodiments, the trusted component is installed at the healthcare data provider, the trusted component programmed and configured to be identified as a component of the healthcare data provider.

In some embodiments, the trusted component is programmed and configured to:

obtain the data provider/application-specific encryption keyset corresponding to each selected healthcare data processor application;

share the public key of the data provider/application-specific keyset with the corresponding selected healthcare data processor application; and encrypt the healthcare data of the healthcare data provider and cause the encrypted healthcare data to be transmitted to the corresponding data processor application.

In some embodiments, the trusted component comprises a private encryption key of the data sharing system installed with the trusted component, wherein the private encryption key is used to sign communications from the healthcare data provider to the authentication server, the communications including the public key of the data provider/application-specific keyset for the authenticating and validating of the public key of the data provider/application-specific keyset.

In some embodiments, the data provider/application-specific keyset is also data-specific, the data pertaining to specific sets of data selected by the data provider for use with the respective data processor application.

In some embodiments, the method further comprises:

providing to the healthcare data provider a selectable option for selecting one or more datasets;

obtaining a selection of the option for the one or more datasets;

at the authentication server, storing a record of the selection of the one or more datasets as corresponding to the data provider/application-specific keyset; and restricting the encrypted healthcare data to be transmitted to the corresponding selected data processor application to the selected one or more datasets.

Some embodiments include a healthcare data sharing system for sharing healthcare data of a healthcare data provider with a healthcare data processor, the system comprising:

a trusted component configured to be trusted by a healthcare data provider as a component of the healthcare data sharing system, the trusted component programmed and configured to:

obtain a data provider/application-specific encryption keyset corresponding to a healthcare data processor application selected by the healthcare data provider, the keyset comprising a private key and a public key;

retain the private key of the data provider/application-specific keyset with the trusted component of the healthcare data provider; and cause the sharing of the public key of the data provider/application-specific keyset with the corresponding selected healthcare data processor application; an authentication server, the authentication server programmed and configured to:

authenticate and validate the public key of the data provider/application-specific keyset as being signed and validated by the healthcare data provider in association with the trusted component;

authenticate and validate the public key of the data provider/application-specific keyset as being signed and validated by the respective selected data processor application.

In some embodiments, at least one of the trusted component or the authentication server is programmed and configured to:

generate and display selectable options of one or more data processor applications at a healthcare data provider; and obtain a selection of one or more data processor applications from the healthcare data provider from the generated display of selectable options;

wherein the provider/application-specific encryption keyset is obtained based on the selection of the one or more data processor applications.

In some embodiments, the trusted component is configured to:

sign the public key of the data provider/application-specific keyset; and share the signed public key with the authentication server and the respective data processor application.

In some embodiments, the trusted component further comprises a private key specific to the trusted component and healthcare data provider distinct from each data provider/application-specific keyset, and wherein the trusted component is configured to sign the public key of the data provider/application-specific keyset with the private key specific to the trusted component and healthcare data provider.

In some embodiments, the authentication server is programmed and configured to:

receive a communication from one of the healthcare data provider or the data processor application indicating that the data provider/application-specific keyset is no longer validated;

in response to receiving the communication, storing a record representing that the data provider/application-specific keyset is invalidated;

receive a communication from one of the healthcare data provider or the data processor application requesting an authentication of the data provider/application-specific keyset;

in response to the communication requesting an authentication, performing a lookup for a record representing that the data provider/application-specific keyset is valid or invalidated, and transmitting a communication to the requesting healthcare data provider or data processor indicating that the respective data provider/application-specific keyset is invalid or unauthenticated based on the lookup.

In some embodiments, the data provider/application-specific keyset is also terms-specific, the terms pertaining to an agreement for use of the healthcare data and the data processor application.

In some embodiments, the data provider/application-specific keyset is also data-specific, the data pertaining to specific sets of data selected by the data provider for use with the respective data processor application.

Some embodiments include a non-transitory computer readable medium comprising programming instructions that, when executed by one or more processors of a data sharing system, cause the data sharing system to execute any of the methods described herein.

BRIEF DESCRIPTION OF THE DRAWINGS

Various objects and advantages of the disclosure will be apparent upon consideration of the following detailed description, taken in conjunction with the accompanying drawings, in which like reference characters refer to like parts throughout, and in which:

FIG. 5 is a flowchart of facilitating the authentication/approval and revocation of the specific contracts/applications provided by a healthcare data processor, according to some embodiments;

DETAILED DESCRIPTION

In some embodiments, a system is configured to provide a healthcare data provider secure sharing of its healthcare data with a selection of external/independent healthcare processing applications. The system can include an interface (e.g., a trusted component) that allows the data healthcare provider to select among a catalogue of data processing applications with which to securely share and process healthcare data. The system may have an authenticator (e.g., a remote authentication server) that authenticates and verifies encryption keys signed by the healthcare data provider and data processor to verify whether data sharing for a specific application has been authorized by the healthcare data provider and data processor, respectively. Verified encryption keys are used to decrypt and encrypt healthcare data and may also be used to provide meta data, including network routing information for directing healthcare data sharing and transmission.

In some embodiments, terms of use (or contracts or agreements) provided by the healthcare data processor are associated with encryption keys that may be signed by the healthcare data provider and verified by the authenticator before healthcare data is authorized for sharing/processing.

Figure 1:
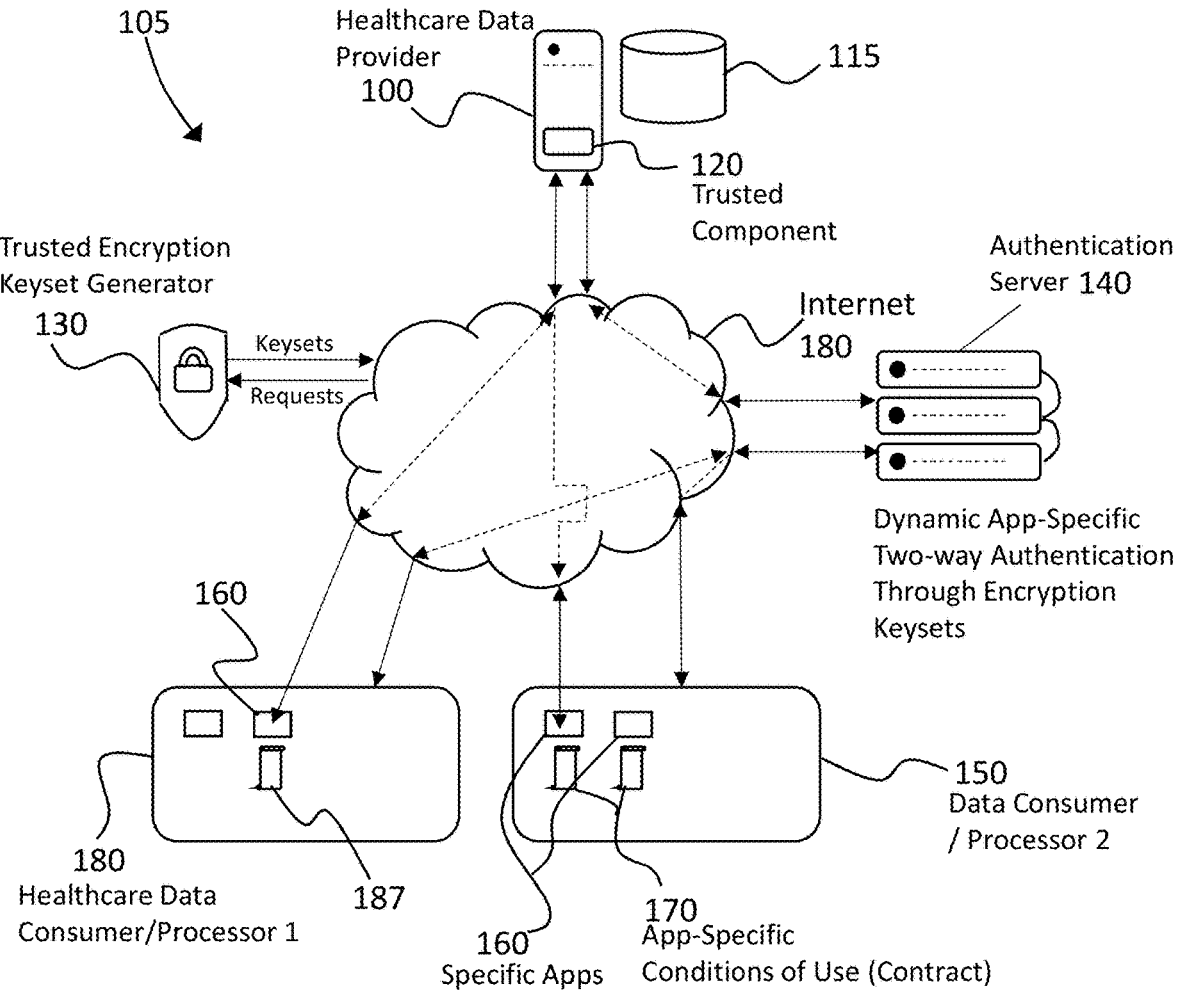
FIG. 1 is an illustrative diagram of healthcare data sharing system for securely sharing healthcare data between a healthcare data provider and a plurality of data processing applications, according to some embodiments.

FIG. 1 is an illustrative diagram of a healthcare data sharing system 105 for securely sharing healthcare data between a healthcare data provider 100 and a plurality of data processing applications 160, according to some embodiments. A healthcare data provider 100 is configured to access and share healthcare data that may include patient electronic medical records, clinical trial data, medical imaging data or other diagnostic data, and/or other types of healthcare data. Data provider 100 stores the records in electronic format (e.g., database(s)) that may be stored in a data server 115 such as connected within a secure, privileged network.

Healthcare data provider 100 is also connected to a wide area network (e.g., the internet) 180 through which it can communicate with elements of the system for sharing healthcare data. Data provider 100 has a trusted component 120 configured to securely process and verify communications between authentication server 140 and data provider 100. The trusted component 120 may be a software module installed on a computing device of data provider 100 and/or may include a separate device (e.g., an encrypted software dongle/key, mobile computing device) directly connected with data provider 100 within its privileged network and is trusted by the authentication server 140 and by the data provider as originating from the same source as the data sharing system/authenticator. In some embodiments, trusted component has a private encryption key securely embedded within it (e.g., itself encrypted) that is used to sign other encryption keys and/or data that may be shared/transmitted (e.g., with authentication server 140 and/or a data processing application 160 as further described herein).

Trusted component 120 may be programmed and configured to authenticate/identify data provider 100 when requested by authentication server 140, to verify authentication server 140, and programmed to process encryption and data sharing with a data processing application 160. In some embodiments, this programming includes obtaining and sharing data provider/application-specific encryption keys and requesting authentication/verification of encryption keys with authentication server 140. Data provider/application-specific encryption keys may be generated and obtained from a trusted keyset generator 130. Data processing applications may be associated with specific terms of use, agreements, and/or contracts 170 and the data provider/application specific encryption keys also specific to terms/agreements/contracts. Trusted component and/or authentication server 140 may be programmed to provide an interface for selecting a specific data processing application (e.g., as shown and described with respect to FIG. 4A), to obtain and share data provider-specific, application-specific, and/or contract/terms-specific encryption keys, to request authentication/verification of encryption keys with authentication server 140, to encrypt healthcare data from the healthcare data provider 100, and to share the encrypted data with a data processing application 160 such as further described herein.

One or more data processing applications 160 are available through WAN 180 (e.g., the Internet) from one or more data processors (e.g., 150A and 150B) to process the healthcare data of data provider 100. Data processors 150A and 150B may host operation of data processing applications 160 such as on an application server device and/or may provide for installation of data processing applications 160 on a device at data provider 100. Data processors 150A and 150B and their applications 160 are configured to operate in coordination with authentication server 140 and trusted component 120, including the receiving of shared, encrypted healthcare data from healthcare data provider 100, and the decrypting and processing of the shared data. The data processing applications may include those that analyze patient records and/or other data from provider 100 to determine diagnosis, treatment(s), and/or assist with clinical research.

When a data processing application 160 is selected for use by healthcare data provider 100, the authentication server 140 and respective data processor (e.g., 150A or 150B) is alerted (e.g., by trusted component 120) and a process of obtaining, signing, and distributing specific encryption keys with respect to the selected application commences.

Data sharing transactions between respective data processors 150A and 150B and data provider 100 are verified and secured by way of communication between the processors and authentication server 140. As further described herein, data provider/application-specific encryption keys are generated (e.g., by key generator 130) for each selected application and used by healthcare data provider 100 to encrypt healthcare data and used by the data processors to decrypt the data. Before an encryption/decryption process occurs, the application-specific keys are to be respectively signed by the data provider 100 (e.g., utilizing trusted component 120) and the data processor/application, after which they are shared with authenticator 140. Authenticator 140 verifies/authenticates the signatures and stores a record of signing/verification as respective permission by each to conduct the encryption, sharing, and decryption. Either of the data provider 100 or data processor 150A or 150B may revoke authorization by communicating the revocation of an application-(and/or data provider and/or contract-)specific key to authenticator 140. In some embodiments, this occurs by communication of the signed key with a notice that the key has been revoked. In response to status requests of permissions from either the data provider or processor (e.g., the authenticity/validity of respective application-specific keys), authenticator 140 performs a lookup for a record representing verification/authentication for a specific data provider and data processing application and responds based on the lookup, depending on whether a record (or lack of a record) indicates that data sharing is permitted or not (e.g., the authenticity/validity or lack thereof of respective application-specific keys).

TABLE I

Retrieval, Selection, and Authentication of Available Data Processing Apps

| Action | Trusted Component (TC) | Authentication Service (AS) | Data Processing Application (app) |
|---|---|---|---|
| TC of Health Care Provider and Authentication Service Verify Each Other/AS Secure channel created | Obtain private TC key, Send AS public TC key | Use public TC key and AS private key | |
| TC queries AS for available data processing Apps | Use private TC key and AS public key | Use public TC key and AS private key | |
| TC retrieves list of available/selected platforms with {app-specific public keys} from AS | Receives and verifies AS-signed app-specific public keys; Present App Status/Menu to Data Provider | Publish currently available, selected, and authenticated apps to TC/Data Provider | |
| Data Provider Selects | 1- TC- specific app- | 5- Verify received | 8 - Receive the |

TABLE I-continued

Retrieval, Selection, and Authentication of Available Data Processing Apps

| Action | Trusted Component (TC) | Authentication Service (AS) | Data Processing Application (app) |
|---|---|---|---|
| Data Processing Application(s) | specific private/public key pair generated; TC signs public key with private TC key 2- Sign app-specific key and store locally; 4- Share TC-signed public app key with AS 9- Share TC-signed TC-specific app-specific public key with AS | Signatures 6- Sign the received TC-signed public app key and store as record 7-Share the received TC-signed public app key with the app 10- Share the TC-signed TC-specific app-specific public key with the specific app, store local copy | TC- signed public app key 11- Receive the TC- signed TC-specific app-specific public key from the AS |

TABLE II

Healthcare Data Sharing Procedure

| Action | Trusted Component (TC) | Authentication Service (AS) | Data Processing Application (app) |
|---|---|---|---|
| Trusted component receives and transforms data from the Data Provider and prepares it for processing by the selected app(s). | 1- Encrypt prepared data with valid/active app-specific public key [TC periodically checks for revocation with AS] 3- Add meta information for routing 4- Sign result with TC-specific, app-specific private key | 2- Update revocation information (verify if app-specific public has been revoked) | |
| Encrypted and signed data is routed to the corresponding app via meta information (which may be signed but unencrypted) Corresponding app processes the data | | 5 - Supports correct routing to corresponding app by allowing AS to verify TC-specific, app-specific signature | 6 - Verify TC-specific app-specific signature (if unknown and at periodic intervals: check Authentication Service for key) 7- Decrypt data using app-specific private key |
| TC periodically retrieves list of revoked apps and revokes related app-specific public keys with AS | Receives and verifies AS (e.g., PKI) signed list of revoked app-specific keys; Revokes revoked app- specific keys; | Transmit status of revoked apps to Data Provider | |

Figure 2:
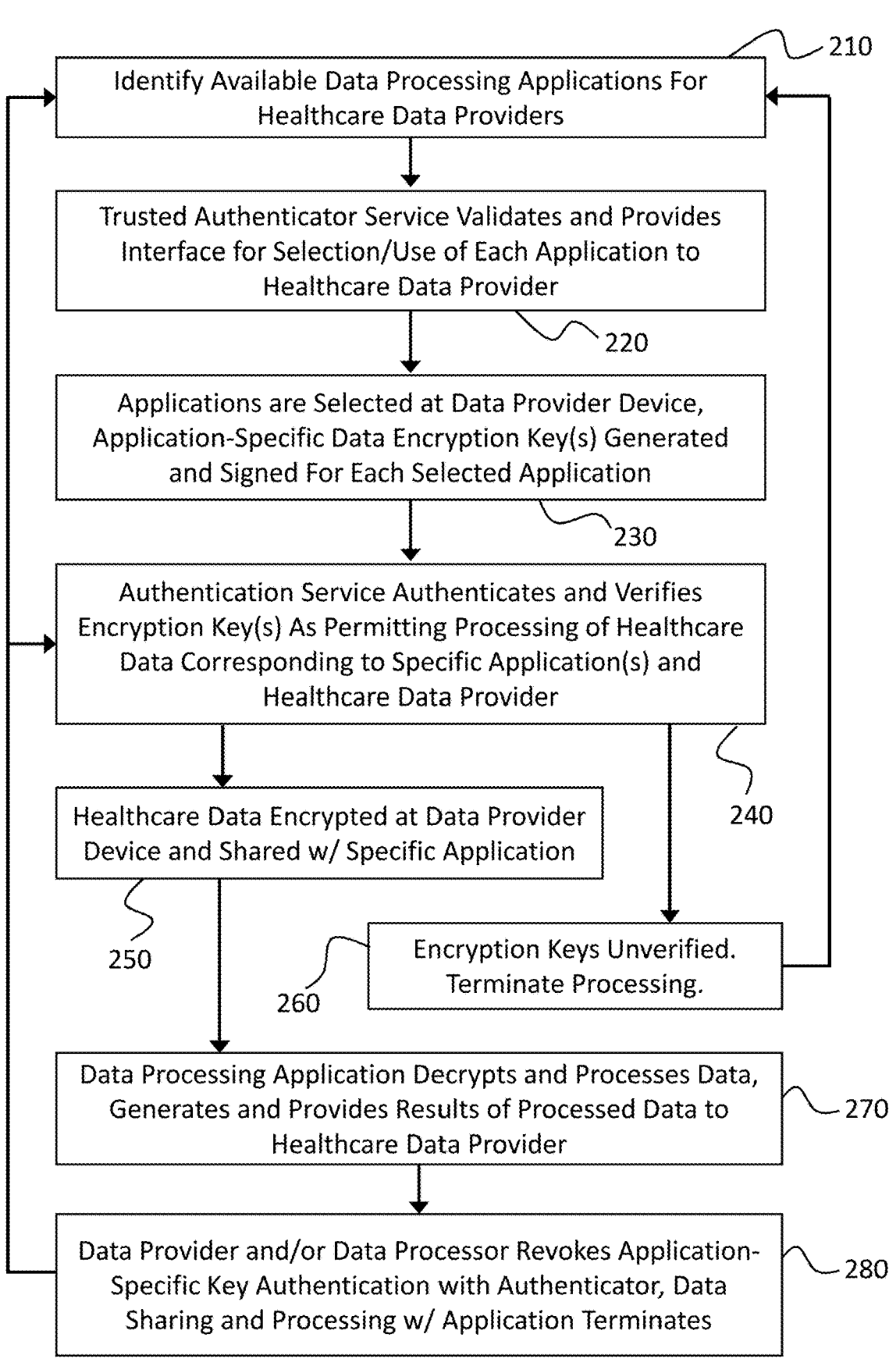
FIG. 2 is a flowchart of a healthcare data sharing system facilitating the secure sharing of healthcare data from a healthcare data provider with a selection of available healthcare data processing applications, according to some embodiments.

FIG. 2 is a flowchart of a healthcare data sharing system facilitating the secure sharing of healthcare data from a healthcare data provider with a selection of available healthcare data processing applications, according to some embodiments. At block 210, the healthcare data sharing system generates and shares a list of available data processing applications (or "apps") with the healthcare data provider. The identification of available data processing applications may performed by querying a set of known healthcare data processors or other known sources for this information (e.g., a third party supplier/vendor). In some embodiments, meta data regarding the data processor applications is provided for each data processor application (e.g., routing information, IP addresses, URLs, domain names).

Figures 4A, 4B:
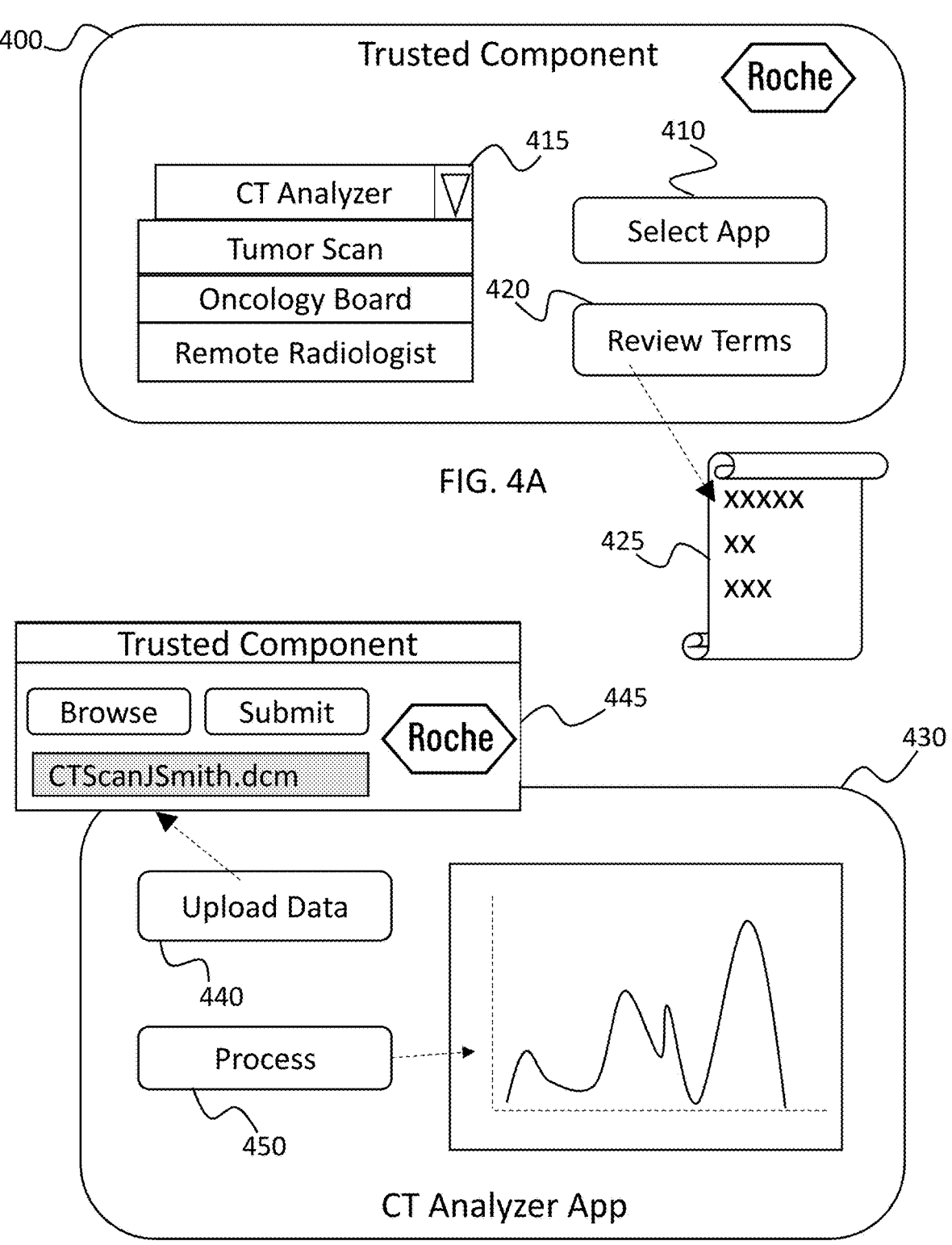
FIG. 4A is an illustrative diagram of a software interface of a healthcare data sharing system for a data provider to select a data processing application, according to some embodiments.
FIG. 4B is an illustrative diagram of a data processing application interface, according to some embodiments.

At block 220, once the information about each of the data processing applications is obtained, a list of the applications is presented to the healthcare data provider by the healthcare data sharing system (e.g., as illustrated in FIG. 4A). In some embodiments, a trusted component (e.g., trusted component 120 of FIG. 1) operates with the healthcare data provider to present the available data processing applications. An authorized operator of the healthcare data provider may select one of the applications for sharing data with the selected data processing application(s) (e.g., as illustrated in FIG. 4B).

At block 230, in response to a selection of one or more of the available data processing applications, an application-specific encryption key for each selected application is signed by the data provider and shared with an authentication service of the healthcare data sharing system. In some embodiments, the trusted component obtains or receives a "public" application-specific encryption key on behalf of the data provider and signs a copy of the key prior to transmitting the signed key to an authenticator (e.g., authentication server 140 of FIG. 1). In some embodiments the application-specific keyset is both data provider-specific and application-specific (data provider/application specific). The respective data processing application (or data processor) is provided access to a corresponding "private" application-specific encryption key for each selected application (and data provider). The data processor may then sign the private encryption key prior to transmitting the signed key to an authentication service (e.g., authentication server) of the healthcare data sharing system, indicating authorization to receive and process data from the respective data provider.

At block 240, the authentication service of the healthcare data sharing system receives the signed application-specific encryption keys from the data provider and data application/processor. The authentication service verifies the signatures of the keys as corresponding to the data provider and data processor. Upon verification of the keys, the authentication service stores a record of the verification/authentication. In some embodiments, the signature corresponding to the data provider originates from the trusted component utilizing a signing key proprietary to the healthcare data sharing system. In some embodiments, the signing key is integrated into a secure software and/or hardware module of the trusted component.

If the authentication service fails to verify the application-specific keys, each of the data provider and data processor may be notified of the failure. In some embodiments, the data provider and/or data processor may request verification of the application-specific keys' authorizations at different times while performing data sharing transactions, such as at least once with respect to each of multiple data sharing transactions. In some embodiments, the trusted component communicates the status request(s) to the authentication service on behalf of the data provider.

At block 250, after authentication of the application-specific key(s), the healthcare data sharing system (e.g., trusted component) receives data from the healthcare data provider and encrypts the data utilizing the data provider's application-specific key. The encrypted healthcare data is then transmitted/shared (e.g., by the trusted component) with the healthcare data processing application/processor.

At block 260, if the application-specific authorizations cannot be verified for the data provider (e.g., by the trusted component), the healthcare data sharing system will not provide sharing of the data provider's healthcare data with the data processing application. The healthcare data provider and data processing application/processor may subsequently engage in authorizing or re-authorizing data sharing between them at block 210.

At block 270, after the data processing application receives the encrypted healthcare data, it decrypts the data using the application-specific encryption key and processes the decrypted data. The data processing application may then share the results of the processing with the healthcare data provider such as by transmitting a report of the results and/or displaying processing results in a user interface (e.g., web page or by way of an application installed at the healthcare data provider as illustrated in FIG. 4B).

At block 280, after authorization of data sharing by the healthcare data provider and/or data processing application, one or both revokes data sharing/processing with the data sharing system for the specific application. This may be performed by transmitting such a revocation message including a respective (signed or unsigned) application-specific key to the healthcare data sharing system. In some embodiments, the revocation is received by an authentication service (e.g., server 140 of FIG. 1), after which the service stores a record (or removes/omits a record), reflecting that data sharing between the healthcare data provider and data processing application is revoked or otherwise unauthorized. After such a revocation, further data sharing transactions may be rejected by the data sharing system until and if authorization is re-established.

In some embodiments, the authentication service is configured and programmed to respond to authentication requests from the data provider and/or data processing application with respect to an application-specific keyset. The authentication service then responds with a transmission indicating that the application-specific keyset is either authenticated/valid or revoked/invalid/unauthenticated respectively. In some embodiments, the authentication service is programmed to automatically update the data provider and/or data processing application when the validity/authentication of a particular application-specific keyset changes.

Figure 3:
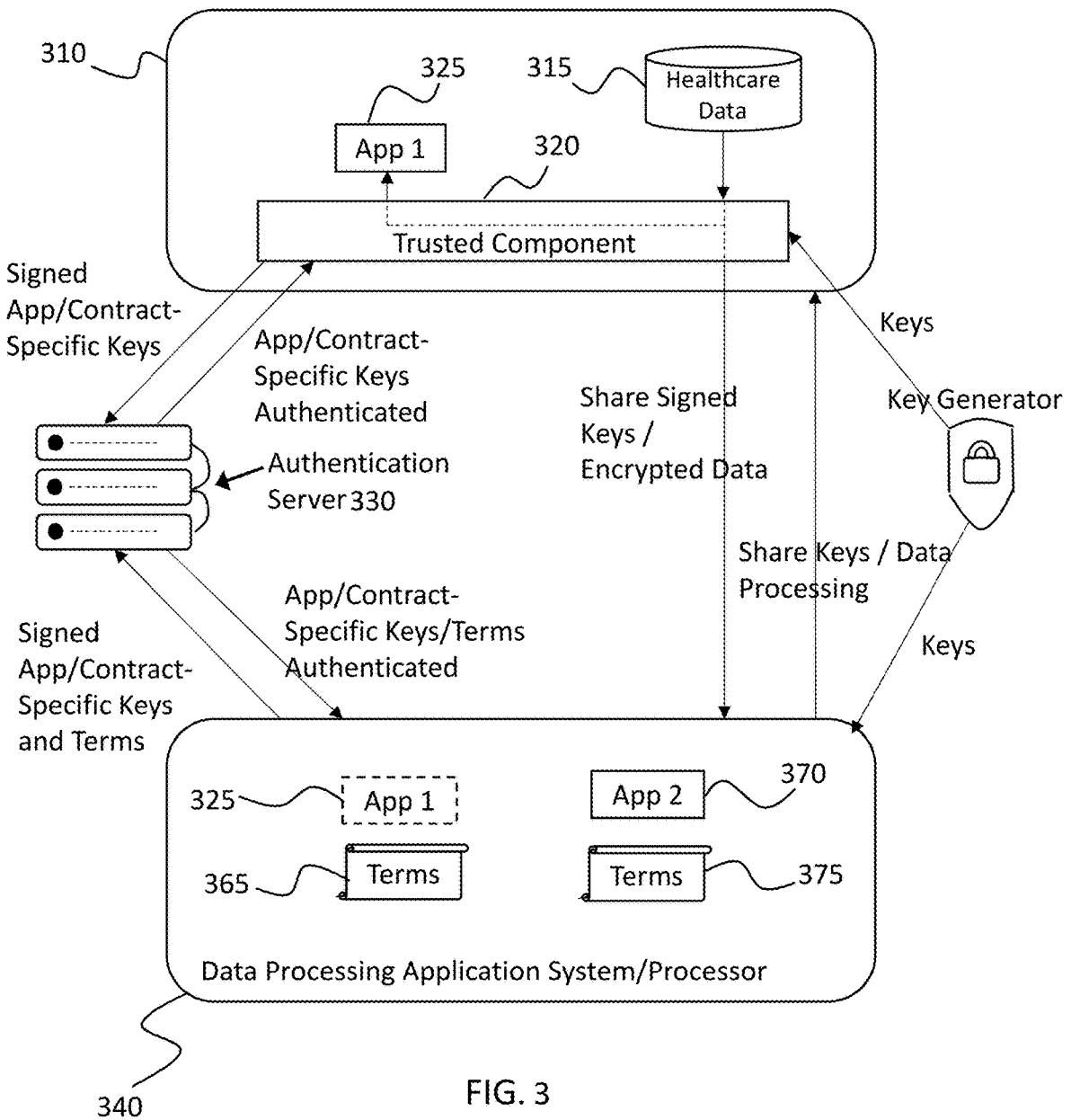
FIG. 3 is an illustrative diagram of a system that facilitates signing authorization of application-specific and contract-specific encryption keys between a healthcare data provider and the provider of a selected data processing application, according to some embodiments.

FIG. 3 is an illustrative diagram of a system that facilitates signing authorization of application-specific and contract-specific encryption keys between a healthcare data provider and the provider of a selected data processing application, according to some embodiments. A healthcare data provider 310 includes a healthcare data source 315 from which it shares healthcare data with a healthcare data processor 340.

The healthcare data sharing system is configured to facilitate sharing and processing of the data provider's data with a data processing application 325 of data processor 340. The data processing application 325 may be a software application installed on the data provider 310 and/or operated remotely at the data processor 340. Such as described further herein, a trusted component 320 of a healthcare data sharing system is integrated with data provider 310 and used to negotiate and secure data sharing and contract transactions between the data provider 310 and data processing application 325.

The healthcare data sharing system, including trusted component 320 and an authentication server 330, obtain information about available data processing applications from data processors, including data processing applications 325 and 370 from data processor 340. In some embodiments, authentication server 330 is configured with information regarding what data processing applications are available. The screening process may involve, for example, a process by the data sharing system that verifies whether data processors and their applications meet a particular level of security and trust. Data processors may communicate to the data sharing system (e.g., authentication sever 330) the availability of their data processing applications and, after a screening process, accept or deny admission of the application for availability within the system. Upon acceptance into the system, authentication server may generate application-specific encryption keys with respect to each of the available applications.

In some embodiments, terms of use or contracts (or agreements) 365 and 375 are provided by the data processors for respective data processing applications 325 and 370. These terms may be made available to the data provider such as through the interface shown in FIG. 4A. In some embodiments, the healthcare data sharing system may screen these contracts and highlight key terms (e.g., data uses, retainment, internal/partner sharing) for review by the data provider within an interface. In some embodiments, screening may include determining whether the contract/terms comply with certain areas of the law (e.g., data privacy laws) or policies (e.g., as requested by the data provider) before allowing the respective application to be available to the healthcare data provider. In some embodiments, the screening includes applying a natural language processor (NLP) and/or machine learning system that reviews the contract in order to identify key terms and/or verify their compliance with applicable laws(s) and/or policies. In some embodiments, the healthcare data sharing system provides an interface for payment to the data processor by the data provider for use of the data processing application.

In some embodiments, contract-specific (e.g., or agreement-specific) encryption keys are generated (e.g., by key generator 350) with respect or pertaining to the contracts/terms and distributed between the data processor and healthcare data provider. To signify an offer of the contract/terms and an acceptance of the offer, the respective data processor and data provider may sign the contract-specific encryption keys in a similar manner to signing the corresponding application-specific key(s) as further described herein. When each of the data provider and processor have shared a signed contract-specific key with authentication server 330, data server 330 stores a record of the signed key. Each of the data provider 310 and processor 340 may also revoke their acceptance of the contract by communicating the revocation to authentication server 330. Before processing each data sharing transaction, the data provider (via trusted component 320) and data processor 340 may verify with the authentication server that the contract is still active and valid as between provider and processor.

FIG. 4A is an illustrative diagram of a software interface 400 of a healthcare data sharing system for a data provider to select a data processing application, according to some embodiments. The interface may be programmed to operate from a trusted component (e.g., trusted component 120 of FIG. 1) that presents available data processing applications (e.g., queried from authentication server 140) to a healthcare data processor. A menu 415 provides a selectable list of available data processing applications. A particular data processing application may be selected for use by the healthcare data provider by using a button 410. In response to toggling button 420, the healthcare data sharing system presents specific terms of a contract 425 associated with a data processing application (e.g., terms 365 and 375 of FIG. 3). In some embodiments, reviewing terms of a contract includes identifying particular types of terms and a contract's compliance with particular laws or policies and presenting the results of the review in an interface for the data provider.

FIG. 4B is an illustrative diagram of a data processing application interface, according to some embodiments. A data processor may provide a processing interface 430 through a data processing application (e.g., data processing applications 160 of FIG. 1) operating on a computing system (e.g., a web interface) of the data processor and/or installed on a computing system of the healthcare data provider that operates in coordination/cooperation with the healthcare data sharing system (e.g., through trusted component 320 of FIG. 3A).

The interface 430 includes a function through which a healthcare data provider shares healthcare data that is activated by toggling button 440. This function invokes a separate interface 445 provided by the healthcare data sharing system that allows an operator of the data provider to select the data to be shared (e.g., from data server 115). Upon (or before) selecting the healthcare data, the healthcare data sharing system may first authenticate/validate use of the data processing application by the healthcare data provider such as by verifying the corresponding application-specific and/or contract-specific encryption keys as further described herein.

After selection of healthcare data and verification that data can be shared with the data processing application (e.g., by verification of application/contract-specific key(s)), the selected healthcare data is encrypted using an application-specific encryption key and shared with the data processing application/processor (e.g., by a trusted component). An operator may then choose to have the data processing application process the data by toggling button 450. The data processing application/processor then decrypts the shared healthcare data using a corresponding application-specific key, processes the unencrypted data, and then presents/shares the results of the processing with the healthcare data provider such as through an interface window 455. The results may be encrypted utilizing an application-specific encryption key and transmitted to the healthcare data provider, after which the data provider decrypts the processing results utilizing an application-specific encryption key.

Figures 4C, 4D:
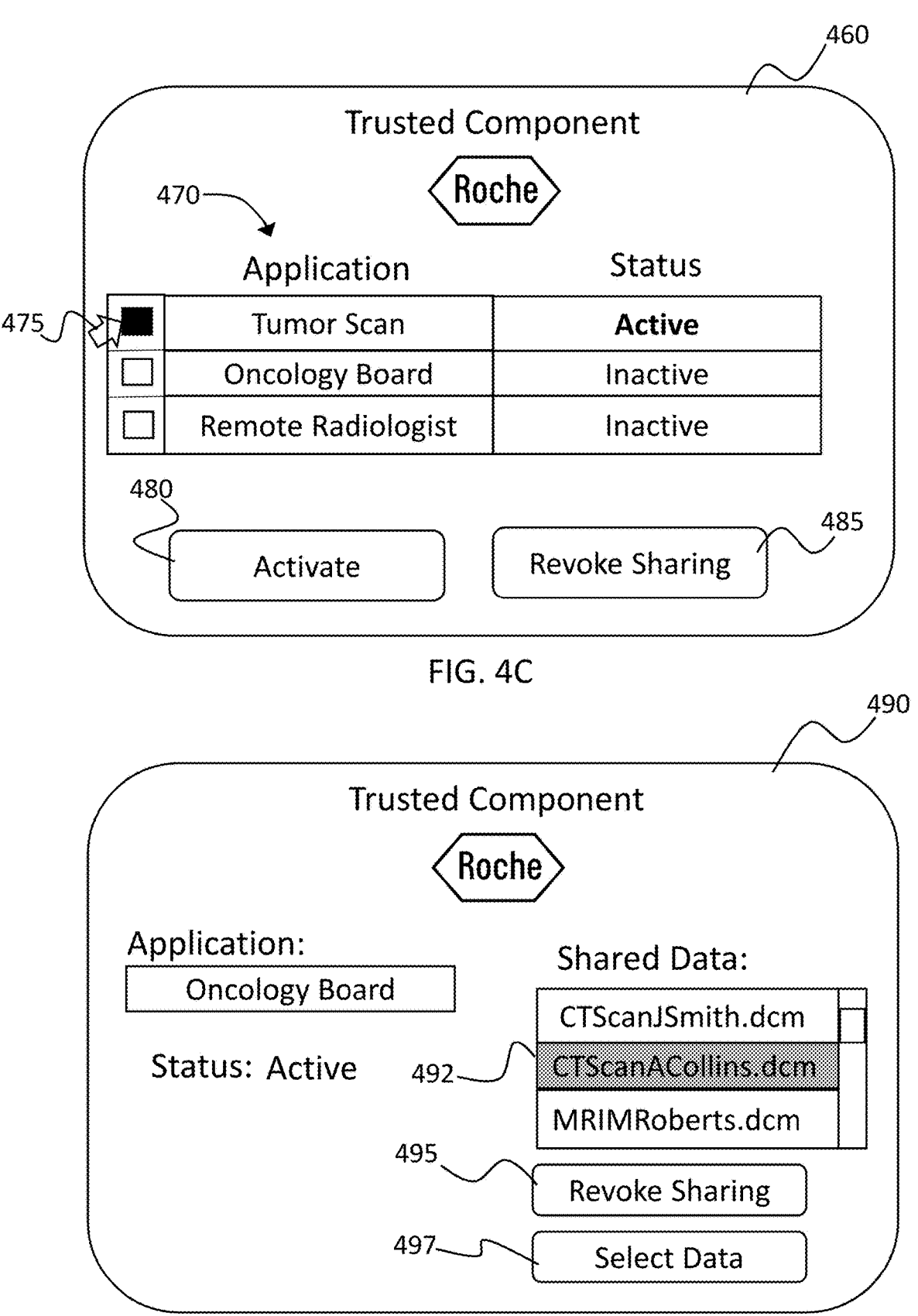
FIG. 4C is an illustrative diagram of a software interface of a healthcare data sharing system for a data provider to authorize and de-authorize data sharing with selected data processing applications.
FIG. 4D is an illustrative diagram of a software interface of a healthcare data sharing system for a data provider to select, authorize, and de-authorize the sharing of particular sets of data with selected data processing applications.

FIG. 4C is an illustrative diagram of a software interface 460 of a healthcare data sharing system for a data provider to authorize and de-authorize data sharing with selected data processing applications. Interface 460 provides a list 470 of active (authorized) and inactive (unauthorized) data processing applications available to the healthcare data provider. The unauthorized data processing applications may include those previously authorized/active and subsequently deactivated (e.g., either by the data provider or data processor). An operator of the healthcare data provider may re-authorize/activate a particular application from control 480 or may revoke authorization of an active application at control 485. The interface 460 may be operated through the trusted component (e.g., trusted component 320) and/or an authentication service (e.g., authentication server 330). As further described herein, authorization causes respective application-specific encryption keys to be authorized (e.g. signed) and shared with authentication service. De-authorization causes a message to be sent to the authentication service (e.g., with the respective signed application-specific key) indicating that data sharing for the specific application has been revoked.

FIG. 4D is an illustrative diagram of a software interface 490 of a healthcare data sharing system for a data provider to select, authorize, and de-authorize the sharing of particular sets of data with selected data processing applications. An operator may select (upon operating control 497) one or more healthcare data files of the data provider to be encrypted and shared with a particular data processing application for processing. In some embodiments, an entire database of records may be shared. The sharing may involve sharing a copy of a file or selecting a file location from which data is directly encrypted and shared. In some embodiments, sharing of data with a data processing application permits changes to the file by the data processor application. An operator may revoke (or cancel) sharing of particular files (e.g., selected at 492) by operating button 495.

FIG. 5 is a flowchart of facilitating the authentication/approval and revocation of the specific contracts/applications provided by a healthcare data processor, according to some embodiments. At block 510, an authenticator of a healthcare data sharing system (e.g., authentication server 140 of FIG. 1) shares a draft contract or the terms of use for a specific data processing application with the healthcare data provider. In some embodiments, the data sharing system screens the contract/terms for compliance with particular policies or laws (e.g., data privacy laws), identifies possible discrepancies related thereto, and may identify and highlight key terms for the healthcare data provider to review (e.g., price, term, warranties). In some embodiments, a contract or terms may correspond to the use of multiple data processing applications (e.g., offered from the same data processor).

At block 520, after reviewing terms of a draft contract at block 510, the healthcare data provider accepts and approves the terms of the application-specific contract (e.g., using the interface of FIG. 4B). Application- and contract-specific encryption keys are made available through the healthcare data sharing system such as further described herein.

At block 530, upon the data provider accepting/agreeing to a contract, the data provider signs corresponding contract-specific and application-specific encryption keys (e.g., through trusted component 320 of FIG. 1). The signed keys are shared with an authentication service of the healthcare data sharing system (e.g., authentication server 330). The data processor (e.g. data processor 340 of FIG. 3) also shares signed contract-specific and application-specific encryption keys with the authentication service.

At block 540, the authentication service authenticates the signatures of the signed contract- and application-specific keys it receives from the healthcare data provider and data processor and stores a record of receiving and authenticating the keys. At block 550, data sharing transactions commence, including the processes of encrypting the data provider's data using the corresponding application-specific encryption key, sharing the data with the data processing application, and decrypting and processing the data such as further described herein.

At block 560, the healthcare data provider has indicated to the authentication service that it is revoking authorization to share its data with the data processing application and/or acceptance of the corresponding contract. The authentication service stores a record of revocation. Indication of revocation may be accomplished, for example, by transmitting (e.g., by way of the trusted component) a message with a signed copy of the corresponding encryption key to the authentication service.

At block 580, as a result of the de-authorization communication from the healthcare provider at block 560, the authentication service responds to later verification requests of the contract-specific and/or application-specific keys by returning a message to the requester (e.g., the trusted component and/or data processing application/processor) that the specific application and/or contract is no longer accepted/authorized for data sharing. Based on this response, the trusted component and/or data processing application ceases data sharing operations with respect to the specific application and/or contract. A data provider may, at a later time, re-authorize a specific application or authorize/accept the same or a different contract for its use.

At block 570, it is the data processing application/processor that revokes use of a specific application and/or contract by making a similar de-authorization communication to the authentication service for a specific application/contract. When the healthcare data provider (e.g., through the trusted component) submits a later verification of the corresponding application/contract-specific key, the authentication service similarly responds indicating that the application/contract-specific keys are no longer active/verified. At block 580, after receiving the negative response from the authentication service, the trusted component ceases healthcare sharing transactions for/under the specific application and/or contract.

Figure 6:
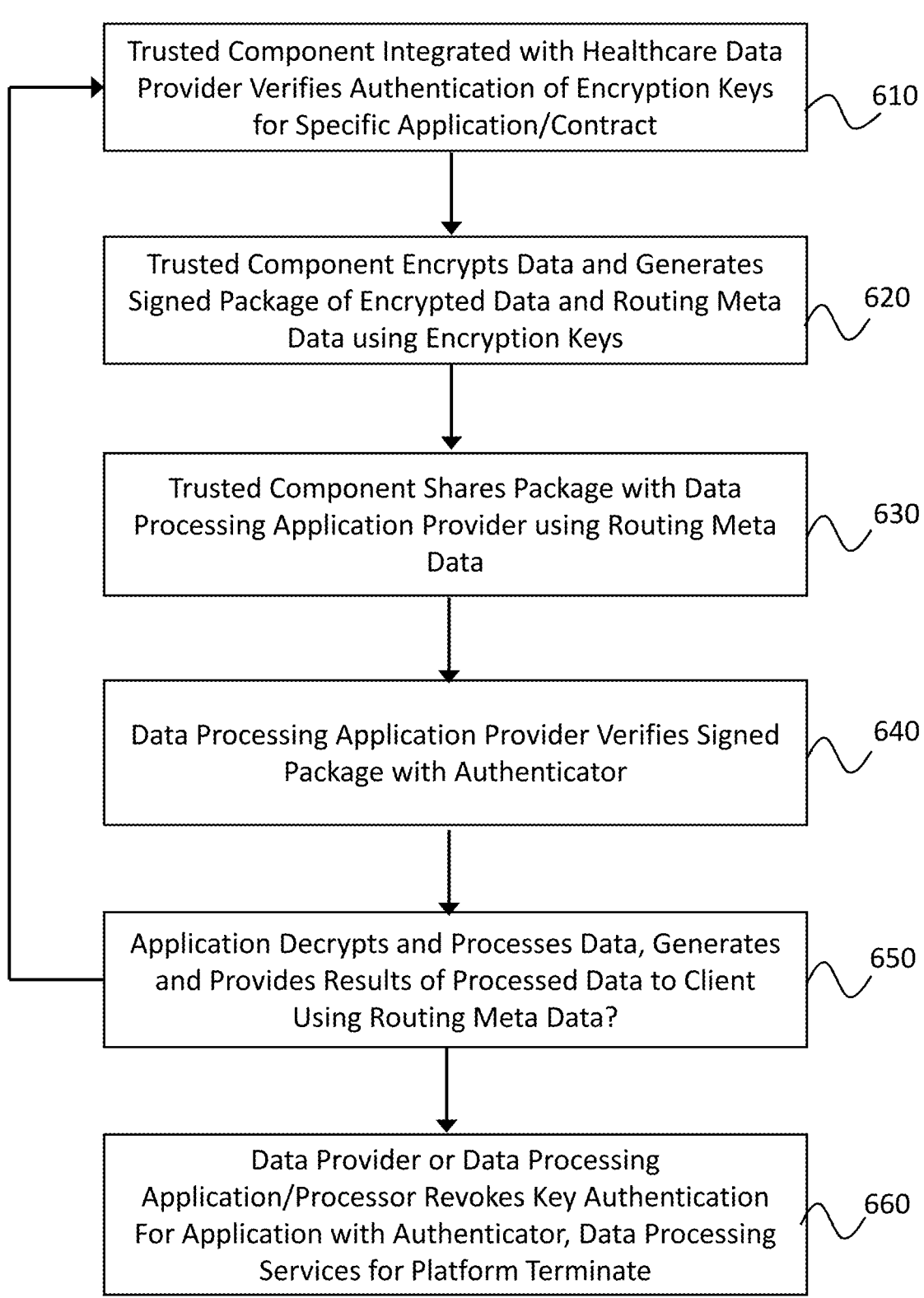
FIG. 6 is a flowchart of process of securely sharing healthcare data between a healthcare data provider and a specific application, according to some embodiments.

FIG. 6 is a flowchart of process of securely sharing healthcare data between a healthcare data provider and a specific application, according to some embodiments. At block 610, a trusted component integrated with a computing device of a healthcare data provider is used to facilitate a data sharing process between a healthcare data provider and a data processing application. In some embodiments, the trusted component is a software application installed on the healthcare data provider's computing device utilizing a secure and trusted installation process approved and/or facilitated by the healthcare data sharing system.

In some embodiments, a hardware element (e.g., a read-only memory flash drive or dongle) from a trusted source is coupled (e.g., by USB/serial port) to the computing device and programmed with a trusted private key or other identification that is trusted/verified by the healthcare data sharing system that is distinct from data provider/application-specific keysets. When the data provider communicates with the data sharing system (e.g., an authentication server), the private key or identification from the hardware is used to identify/verify the healthcare data provider (e.g., by signing communications) with the healthcare data sharing system. The trusted component may also be configured to verify components of the data sharing system (e.g., authentication server) such as by verifying (e.g., using a public key) communications signed by the data sharing system configured with its own private key.

After the trusted component is installed with the healthcare data sharing provider, software installed with the trusted component (or separately such as at a web server) provides an interface for the healthcare data provider to select one or more data processing applications available for processing healthcare data (e.g., FIGS. 4A-4D). Once the application(s) are selected, respective data provider/application-specific keysets are generated and accessed by the trusted component such as further described herein. Before encrypting and sharing data, the trusted component verifies/authenticates a signed public key of the data provider/application-specific keyset within the healthcare data sharing system such as with an authentication service as further described herein. The authentication process can be used to verify that the respective data processing application is still available/authenticated for processing data and obtain updated meta data such as forwarding information (e.g., URL, IP address) for where to share data.

At block 620, after the data sharing service has authenticated the specific data sharing application for use, healthcare data from the data provider is gathered and encrypted (e.g., using an application-specific encryption key as further described herein) and the trusted component is used to sign/verify the encrypted healthcare data, along with other meta data used to perform the data sharing transaction. In some embodiments, the meta data includes routing information (e.g., domain names, URLs, IP addresses) about the destination (e.g., data processors 150A or 150B) and/or return location for the processed data/report. In some embodiments, the trusted component includes software installed on a computing device which signs the package using a private encryption key associated with the healthcare data provider.

At block 630, upon authentication/verification of a public key of the respective data provider/application-specific keyset, the data provider (e.g., using the trusted component) encrypts selected data of the data provider using a private key of the keyset. A package is generated (e.g., by the trusted component) including the encrypted data with meta data (e.g., routing information for forwarding the data to a particular data processor, for where to return results of processing, identification of the data, and/or instructions for processing the data), the package is signed using the private key of the keyset and is transmitted to (or otherwise shared with) the data processing application/processor.

At block 640, after receiving the encrypted package, the data processor/processing application verifies/authenticates the package with an authentication service (e.g., at authentication server 140 with the package's signature). At block 650, once authenticated, the data processing application decrypts the encrypted data using a public key of the data provider/application-specific keyset, processes the data (e.g., analyzes/modifies), generates processing results (e.g., a report including data analytics, graphical charts, diagnosis, predictions, reports, newly processed data, etc.), and then shares (e.g., transmits or makes available) the results of the processing with the data provider (or other designated recipient). In some embodiments, meta data provided with the package (e.g., data characteristics, processing instructions, URLs, domain names, IP addresses) is used to direct the processing and/or generation/sharing of the results/reports of the processing. In some embodiments, before sharing, the results of the processing are first encrypted using an application-specific encryption key corresponding to the healthcare data provider.

Data sharing/processing may continue until one of the healthcare data provider or data processor/processing application revokes authorization at block 660. Such as further described herein, revocation may be accomplished by transmitting a revocation message with an application-specific key and/or other identification associated with the healthcare data provider.

Figure 7:
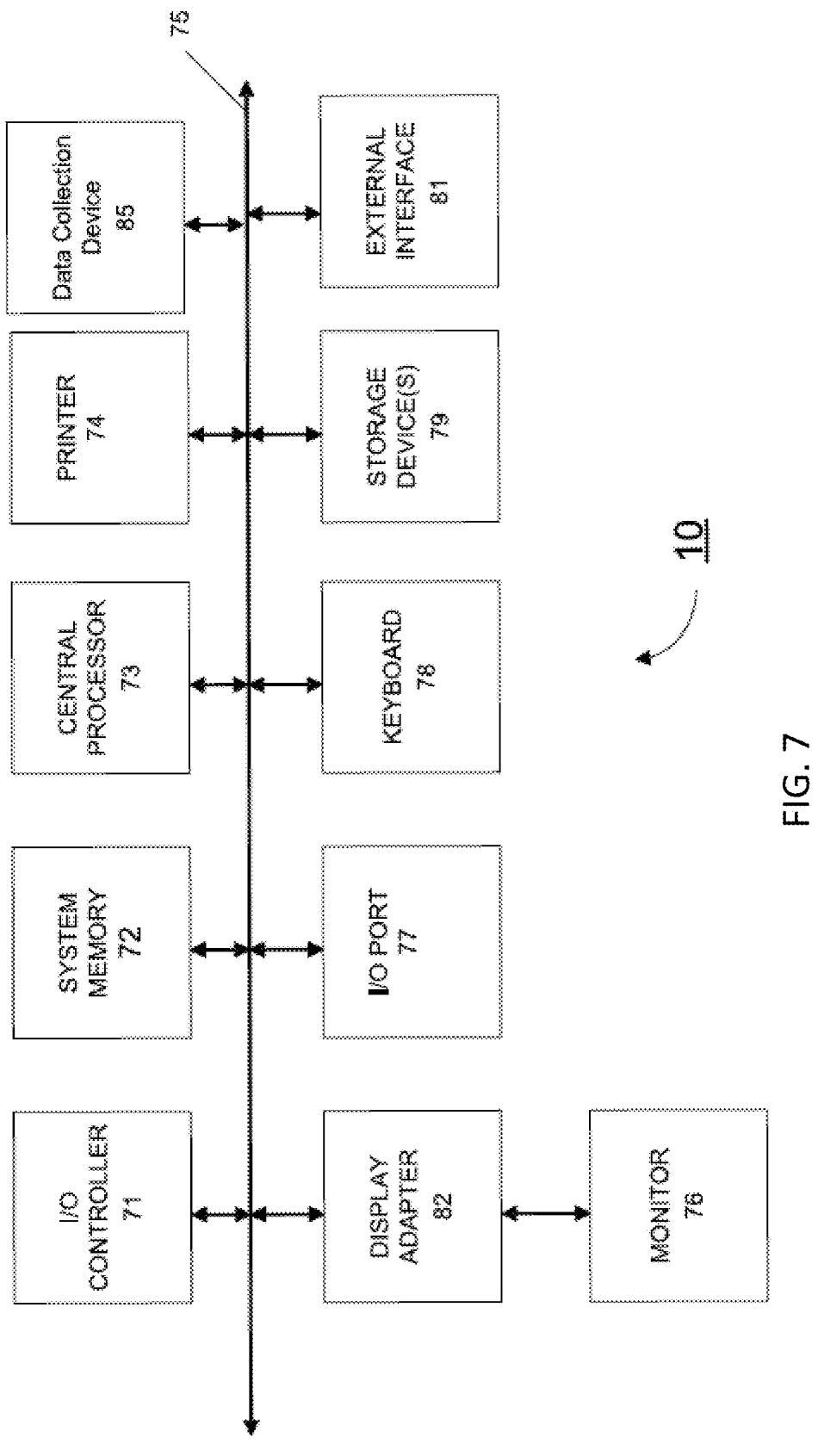
FIG. 7 is an illustrative diagram of computing devices and processing components of a system for securely sharing healthcare data, according to some embodiments.

FIG. 7 is an illustrative diagram of computing devices and processing components of a system for securely sharing healthcare data, according to some embodiments.

The above-described embodiments of the present disclosure are presented for purposes of illustration and not of limitation, and the present disclosure is limited only by the claims which follow. Furthermore, it should be noted that the features and limitations described in any one embodiment may be applied to any other embodiment herein, and flowcharts or examples relating to one embodiment may be combined with any other embodiment in a suitable manner, done in different orders, or done in parallel. In addition, the systems and methods described herein may be performed in real time. It should also be noted, the systems and/or methods described above may be applied to, or used in accordance with, other systems and/or methods.

Any of the computer systems mentioned herein may utilize any suitable number of subsystems. Examples of such subsystems are shown in FIG. 7 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices. In some embodiments, a cloud infrastructure (e.g., Amazon Web Services), a graphical processing unit (GPU), etc., can be used to implement the disclosed techniques.

The subsystems shown in FIG. 7 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C #, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above. A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover reference to a "first" or a "second" component does not limit the referenced component to a particular location unless expressly stated.

All patents, patent applications, publications, and descriptions mentioned herein are incorporated by reference in their entirety. None is admitted to be prior art.

What is claimed is:

1. A computer implemented method, for a healthcare data sharing system to share healthcare data from a healthcare data provider with a healthcare data processor application, comprising:
identifying one or more healthcare data processor applications;
generating and displaying, via an interface of a trusted component associated with the healthcare data provider, selectable options of the one or more healthcare data processor applications, wherein the trusted component comprises a software application executed by at least one computing system based on instructions stored in a computer-readable medium;
obtaining a selection of the healthcare data processor application, selected from the one or more healthcare data processor applications, from the healthcare data provider via the interface of the trusted component;

obtaining a data provider/application-specific encryption keyset corresponding to the healthcare data processor application, the data provider/application-specific encryption keyset comprising a private key and a public key;
retaining the private key of the data provider/application-specific encryption keyset with the trusted component;
sharing the public key of the data provider/application-specific encryption keyset with the healthcare data processor application;
at an authentication server of the healthcare data sharing system, authenticating and validating the public key of the data provider/application-specific encryption keyset as being signed and validated using the trusted component and being signed and validated by the healthcare data processor application; and
in response to authenticating and validating the public key of the data provider/application-specific encryption keyset, causing the healthcare data of the healthcare data provider to be encrypted using the private key of the data provider/application-specific encryption keyset, and causing the encrypted healthcare data to be transmitted to the healthcare data processor application.

2. The computer implemented method according to claim 1, wherein sharing the public key of the data provider/application-specific encryption keyset comprises:
signing the public key using the trusted component; and
transmitting the signed public key to the healthcare data processor application.

3. The computer implemented method according to claim 1, further comprising:
transmitting the signed public key to the authentication server; and
at the authentication server, storing a record of receiving the signed public key in order to authenticate and validate the public key of the data provider/application-specific encryption keyset as being signed and validated by the healthcare data provider using the trusted component.

4. The computer implemented method according to claim 1, further comprising:
at the authentication server, receiving a communication from one of the healthcare data provider or the healthcare data processor application indicating that the data provider/application-specific encryption keyset is no longer validated; and
in response to receiving the communication, ceasing to cause the encrypted healthcare data to be transmitted to the healthcare data processor application.

5. The computer implemented method according to claim 1, wherein the data provider/application-specific encryption keyset is also terms-specific, based on a set of terms pertaining to an agreement for use of the healthcare data and the healthcare data processor application;
wherein the set of terms relate to use of the healthcare data processor application and a selectable option for accepting the set of terms is provided to the healthcare data provider wherein, in response to obtaining a selection accepting the set of terms by the healthcare data provider, the public key of the data provider/application-specific and terms-specific encryption keyset is caused to be signed using the trusted component.

6. The computer implemented method according to claim 1, wherein the trusted component is installed at the at least one computing system, the at least one computing system is associated with the healthcare data provider, the trusted component is programmed and configured to be identified as a component of the healthcare data provider, and the trusted component is programmed to:

obtain the data provider/application-specific encryption keyset corresponding to the healthcare data processor application;

share the public key of the data provider/application-specific encryption keyset with the healthcare data processor application; and encrypt the healthcare data of the healthcare data provider and cause the encrypted healthcare data to be transmitted to the healthcare data processor application.

7. The computer implemented method according to claim 1, wherein the trusted component is configured to use a private encryption key of the healthcare data sharing system, installed with the trusted component, to sign communications from the healthcare data provider to the authentication server, the communications including the public key of the data provider/application-specific encryption keyset for the authenticating and validating of the public key of the data provider/application-specific encryption keyset.

8. The computer implemented method according to claim 1, wherein the data provider/application-specific encryption keyset is also data-specific to specific sets of data selected by the healthcare data provider for use with the healthcare data processor application.

9. The computer implemented method according to claim 1, further comprising:

providing to the healthcare data provider a selectable option for selecting one or more datasets;

obtaining a selection of the one or more datasets;

at the authentication server, storing a record of the selection of the one or more datasets as corresponding to the data provider/application-specific encryption keyset; and restricting the encrypted healthcare data, to be transmitted to the healthcare data processor application, to the selected one or more datasets.

10. A healthcare data sharing system, for sharing healthcare data of a healthcare data provider with a healthcare data processor application, comprising:

a trusted component configured to be trusted by the healthcare data provider as a component of the healthcare data sharing system, wherein the trusted component comprises a software application, executed by at least one computing system based on instructions stored in a computer-readable medium, that is programmed and configured to:

obtain a data provider/application-specific encryption keyset corresponding to the healthcare data processor application selected by the healthcare data provider, the data provider/application-specific encryption keyset comprising a private key and a public key;

retain the private key of the data provider/application-specific encryption keyset with the trusted component; and cause sharing of the public key of the data provider/application-specific encryption keyset with the healthcare data processor application; and an authentication server, the authentication server being programmed and configured to:

authenticate and validate the public key of the data provider/application-specific encryption keyset as being signed and validated by the healthcare data provider using the trusted component; and authenticate and validate the public key of the data provider/application-specific encryption keyset as being signed and validated by the healthcare data processor application.

11. The healthcare data sharing system according to claim 10, wherein at least one of the trusted component or the authentication server is programmed and configured to:

generate and display, via an interface, selectable options of one or more healthcare data processor applications; and obtain a selection of the healthcare data processor application from the healthcare data provider via the selectable options displayed via the interface, wherein the data provider/application-specific encryption keyset is obtained based on the selection of the healthcare data processor application.

12. The healthcare data sharing system according to claim 10, wherein the trusted component is configured to use a second private key, specific to the trusted component and the healthcare data provider and distinct from the data provider/application-specific encryption keyset, to sign the public key of the data provider/application-specific encryption keyset with the second private key specific to the trusted component and the healthcare data provider.

13. The healthcare data sharing system according to claim 12, wherein the authentication server is programmed and configured to:

receive a first communication from one of the healthcare data provider or the healthcare data processor application indicating that the data provider/application-specific encryption keyset is no longer validated;

in response to receiving the first communication, storing a record representing that the data provider/application-specific encryption keyset is invalidated;

receive a second communication from one of the healthcare data provider or the healthcare data processor application requesting an authentication of the data provider/application-specific encryption keyset; and in response to the second communication requesting an authentication, performing a lookup for the record representing that the data provider/application-specific encryption keyset is valid or invalidated, and transmitting a third communication to the requesting healthcare data provider or healthcare data processor application indicating that the respective data provider/application-specific encryption keyset is invalid or unauthenticated based on the lookup.

14. The healthcare data sharing system according to claim 10, wherein the data provider/application-specific encryption keyset is also terms-specific, based on a set of terms pertaining to an agreement for use of the healthcare data and the healthcare data processor application.

15. The healthcare data sharing system according to claim 10, wherein the data provider/application-specific encryption keyset is also data-specific to specific sets of data selected by the healthcare data provider for use with the healthcare data processor application.

16. The healthcare data sharing system of claim 10, wherein sharing the public key of the data provider/application-specific encryption keyset comprises:

signing the public key using the trusted component; and transmitting the signed public key to the healthcare data processor application.

17. The healthcare data sharing system of claim 10, wherein the authentication server is configured to store a record of receiving the signed public key in order to authenticate and validate the public key of the data provider/ application-specific encryption keyset as being signed and validated by the healthcare data provider using the trusted component.

18. The healthcare data sharing system of claim 10, wherein the authentication server is configured to:

receive a communication from one of the healthcare data provider or the healthcare data processor application indicating that the data provider/application-specific encryption keyset is no longer validated; and in response to receiving the communication, ceasing to cause the encrypted healthcare data to be transmitted to the healthcare data processor application.

19. The healthcare data sharing system of claim 10, wherein the authentication server is programmed to:

obtain a selection of one or more datasets;

store a record of the selection of the one or more datasets as corresponding to the data provider/application-specific encryption keyset; and restrict the encrypted healthcare data, to be transmitted to the healthcare data processor application, to the selected one or more datasets.

20. The healthcare data sharing system of claim 10, wherein the trusted component is configured to:

sign the public key of the data provider/application-specific encryption keyset; and share the signed public key with the authentication server and the healthcare data processor application.

\* \* \* \* \*